United States Patent [19]

Grollier et al.

[11] Patent Number: 4,597,962

[45] Date of Patent: Jul. 1, 1986

[54] HAIR-CARE COMPOSITION AND HAIR TREATMENT PROCESS

[75] Inventors: Jean F. Grollier, Paris; Claude Dubief, Le Chesnay; Daniele Cauwet, Paris, all of France

[73] Assignee: L'Oreal, Paris, France

[21] Appl. No.: 625,627

[22] Filed: Jun. 28, 1984

[30] Foreign Application Priority Data

Jul. 1, 1983 [LU] Luxembourg ............................ 84894

[51] Int. Cl.$^4$ .......................... A61K 7/06; A61K 7/08; A61K 7/09; A61K 9/12
[52] U.S. Cl. ........................................ 424/47; 424/62; 424/70; 424/71; 424/72
[58] Field of Search ............... 424/70, 184, 71, 72, 424/47

[56] References Cited

U.S. PATENT DOCUMENTS

| 4,185,087 | 1/1980 | Morlino | 424/70 |
| 4,217,914 | 8/1980 | Jacquet et al. | 424/78 |
| 4,421,769 | 12/1983 | Dixon | 424/184 |

FOREIGN PATENT DOCUMENTS

| BS1991M | 9/1963 | France | 424/184 |
| 2318268 | 2/1977 | France | 424/70 |
| 48-19941 | 6/1973 | Japan | 424/184 |
| 0142542 | 12/1978 | Japan | 424/184 |
| 0016405 | 2/1981 | Japan | 424/70 |
| 0167799 | 12/1981 | Japan | 424/70 |
| 0077920 | 5/1983 | Japan | 424/70 |
| 0092808 | 7/1983 | Japan | 424/70 |
| 802467 | 10/1958 | United Kingdom | 424/184 |
| 2039512 | 8/1980 | United Kingdom | 424/184 |
| 2058103 | 4/1981 | United Kingdom | 424/70 |
| 2098624 | 11/1982 | United Kingdom | 424/70 |
| 2131821 | 6/1984 | United Kingdom | 424/70 |

Primary Examiner—Dale R. Ore
Attorney, Agent, or Firm—Fleit, Jacobson, Cohn & Price

[57] ABSTRACT

A cosmetic composition for the treatment and care of hair, containing (a) at least one cationic surface-active agent which can be dispersed in water, (b) at least one water-soluble quaternized cationic polymer of the ionene type and (c) at least one cationic silicone polymer is disclosed.

13 Claims, No Drawings

HAIR-CARE COMPOSITION AND HAIR TREATMENT PROCESS

The present invention relates to cosmetic compositions for the treatment and care of hair, containing (a) at least one cationic surface-active agent which can be dispersed in water, (b) at least one water soluble quaternised cationic polymer of the ionene type and (c) at least one cationic silicone polymer.

It is well known that hair is generally sensitive to atmospheric conditions, as well as to treatments such as bleaching, permanent waving and/or dyeing, with the result that hair is often difficult to untangle and dress.

One of the means which is widely employed for improving the untangling and the softness of sensitised hair consists of the use of cationic surface-active agents.

The use of cationic surface-active agents however has the disadvantage of making the hair heavier and giving it a greasy appearance.

These disadvantages are emphasised in the case of fine hair which is lacking in body, liveliness and form-retention.

It has already been proposed to improve the untangling and the softness of hair by using cationic polymers which do not have the disadvantage of making hair heavier while having durable effects. However, the untangling which is obtained is inferior to that imparted by a cationic surface-active agent.

Among the cationic polymers which have already been recommended for hair conditioning, we have already described quaternised polymers of the ionene type, as, for example, in French Pat. No. 2,270,846. These polymers facilitate the untangling of wet, natural, bleached or permanent-waved hair and help remove faults from hair sensitised by treatments such as bleaching, permanent waving and/or dyeing, while not making dry hair heavier, and consequently making it easier to obtain hairstyles with body, while retaining liveliness and glossy appearance.

There have also been proposed compositions of a cationic surface-active agent with a cationic polymer.

It is not possible to obtain the maximum possible effect from these combinations of the cationic surface-active agent and cationic polymer, because in the majority of cases the deposition of the cationic surface active agent slows down the deposition of the cationic polymer.

There have been proposed, in French Patent Application No. 2,463,612, hair-care compositions combining cationic polymers of the MERQUAT 100 and 550, or ONAMER type, and/or quaternised polyvinylpyridines with cationic silicone polymers of the Amodimethicone type to produce some durability of the cosmetic properties.

However, these compositions still have the disadvantage that they do not adequately provide the required properties of untangling, liveliness and form-retention.

We have surprisingly discovered that by associating in a hair-care cosmetic composition (a) a cationic surface-active agent which can be dispersed in water, (b) a water-soluble quaternised polymer of the ionene type, and (c) a cationic silicone polymer, preferably of the Amodimethicone type, an optimum and simultaneous deposition of these three components on the hair was promoted and a cosmetic composition was obtained which was noticeably superior to those known hitherto, insofar as the properties of untangling, softness, brilliance, lightness, liveliness, body, pleasant touch and appearance were concerned, while retaining the advantage of not making the hair heavier, and making it antistatic, these cosmetic effects being moreover durable.

In the case of sensitised hair, the composition according to the invention makes hair more resistant to repeated applications of products which modify the keratin fibre such as colorants, bleaches, permanent waving compositions and hair-straighteners.

Thus, the invention provides a cosmetic hair-care composition containing (a) at least one cationic surface-active agent which can be dispersed in water, (b) at least one water-soluble quaternised polymer of the ionene type and (c) at least one cationic silicone polymer.

The invention also provides a process for treating hair comprising applying to the hair an appropriate quantity of a composition as referred to above.

In the following description, the term "lower" group, means a group containing 1 to 6 carbon atoms, preferably 1 to 4 carbon atoms.

The cationic surface-active agents to be used according to the invention are compounds which can be dispersed in water, and are preferably chosen from the compounds of formula (I)

in which:

(1) $R_1$ denotes a group of formula:

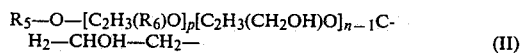

where
$R_5$ denotes a linear or branched, saturated or unsaturated aliphatic radical, preferably an alkyl radical of 4 to 20 carbon atoms;
$R_6$ denotes:
(i) an alkyl radical, preferably a linear alkyl radical
(ii) a linear or branched alkoxymethyl radical;
(iii) a linear alkenyloxy radical
the alkyl or alkenyl parts of these radicals representing $R_6$ preferably containing 4 to 20 carbon atoms;
p denotes an integer or decimal number from 1 to 2.5 and represents a statistical mean value;
n denotes an integer or decimal number from 2 to 20 and preferably 2 to 15 and represents a statistical mean value;
$R_2$ denotes an alkyl or hydroxylalkyl radical, preferably containing from 1 to 3 carbon atoms;
$R_3$ and $R_4$, which may be identical or different, denote an alkyl or hydroxyalkyl radical, preferably containing from 1 to 3 carbon atoms and more preferably a methyl, ethyl, isopropyl or hydroxyethyl radical or $R_3$ and $R_4$ form, together with the nitrogen atom to which they are attached, a 5- or 6-membered heterocyclic ring, preferably a heterocyclic pyrrolidine, piperidine, morpholine or N-methylpiperazine ring,
$X^\ominus$ denotes an anion, preferably a methylsulphate, methanesulphonate, p-toluenesulphonate, bromide, chloride or iodide anion; or
(2) $R_2$ and $R_3$ denote methyl,
$R_1$ and $R_4$ having then the following meanings:

(i) $R_1$ and $R_4$ denotes a linear saturated aliphatic radical, preferably an alkyl radical containing from 12 to 22 carbon atoms or an aliphatic radical, preferably derived from tallow fatty acids, preferably containing from 14 to 22 carbon atoms, (ii) $R_1$ denotes a linear saturated aliphatic radical, preferably an alkyl radical containing from 14 to 22 carbon atoms, and $R_4$ denotes methyl or benzyl, (iii) $R_1$ denotes an alkylamidopropyl radical, the alkyl group of which preferably contains 14 to 22 carbon atoms and $R_4$ denotes an alkyl acetate group, the alkyl group of which preferably contains 12 to 16 carbon atoms.

$X^\ominus$ denotes an anion, such as a halide or $CH_3SO_4^\ominus$; or (3) $R_1$ denotes an alkylamidoethyl and/or alkenylamidoethyl group in which the alkyl and/or alkenyl radical, preferably containing from 14 to 22 carbon atoms, is derived from tallow fatty acids and $R_2$ and $R_3$ form with the nitrogen atom to which they are attached a substituted heterocyclic ring of the 4,5-dihydro-imidazole type, such as a 2-alkyl (derived from tallow fatty acids), 4,5-dihydroimidazole, heterocyclic ring, $R_4$ denotes an alkyl group of 1 to 4 carbon atoms, preferably a methyl group, and $X^\ominus$ denotes a $CH_3SO_4^\ominus$ anion.

An example of such a cationic surface-active agent is the compound sold under the name "REWOQUAT W 7500".

Among the cationic surface-active agents of the formula (I) the following compounds are preferred, in which:

(a)

$R_1$ denotes
$$R_5-O-[C_2H_3(R_6)O]_p[C_2H_3(CH_2OH)O]_n- _1-CH_2-CHOH-CH_2- \quad (II)$$

where
$R_5$ denotes $C_8H_{17}$ or $C_{10}H_{21}$,
$R_6$ denotes $C_{14}H_{29}$ or $C_{16}H_{33}$
p denotes the number 1,
n denotes an integer or decimal number from 2 to 5,
$R_2$ denotes a methyl radical,
$R_3$ and $R_4$, together with the nitrogen atom to which they are attached, denote a morpholino ring,
$X^\ominus$ denotes $CH_3SO_4^\ominus$ or $CH_3SO_3^\ominus$; or (b)

$R_1$ denotes
$$C_{10}H_{21}-O-[C_2H_3(C_{14}H_{29})O]-[C_2H_3(CH_2OH)O]-CH_2-CHOH-CH_2- \quad (III)$$

$R_2$ denotes a methyl radical,
$R_3$ and $R_4$, together with the nitrogen atom to which they are attached, denote a morpholino heterocyclic ring,
$X^\ominus$ denotes $CH_3SO_3^\ominus$; or (c)

$R_1$ denotes
$$C_{10}H_{21}-O-[C_2H_3(C_{14}H_{29})O]-[C_2H_3(CH_2OH)O]_4-CH_2-CHOH-CH_2- \quad (IV)$$

$R_2$ denotes a methyl radical,
$R_3$ and $R_4$, together with the nitrogen atom to which they are attached, denote a morpholino heterocyclic ring,
$X^\ominus$ denotes $CH_3SO_3^\ominus$; or (d) $R_1$ and $R_4$ each denote a mixture of alkenyl and/or alkyl radicals, preferably derived from tallow fatty acids, having from 14 to 22 carbon atoms,
$R_2$ and $R_3$ denote a methyl radical, and
$X^\ominus$ denotes $Cl^\ominus$; or (e) $R_1$ denotes an alkylamidoethyl group and/or an alkenylamidoethyl group where the alkyl and/or alkenyl radical contains from 14 to 22 carbon atoms, derived from tallow fatty acids, $R_2$ and $R_3$ form, together with the nitrogen atom to which they are attached, a 2-alkyl (derived from tallow fatty acids) 4,5-dihydroimidazole heterocyclic ring; $R_4$ denotes an alkyl group of 1 to 4 carbon atoms.

The quaternised polymers of the ionene type to be used according to the invention are preferably water-soluble quaternary polyammonium compounds having repeat units of formula:

(V)

in which $R_7$, $R_8$, $R_9$ and $R_{10}$, which may be identical or different, represent aliphatic, alicyclic or arylaliphatic radicals containing at most 20 carbon atoms or lower hydroxyaliphatic radicals or $R_7$ and $R_8$, and $R_9$ and $R_{10}$, together or separately, form with the nitrogen atoms to which they are attached heterocyclic rings which may contain a second hetero-atom other than nitrogen, or $R_7$, $R_8$, $R_9$ and $R_{10}$ represent a group:

(VI)

in which $R'_3$ denotes hydrogen or a lower alkyl group and $R'_4$ denotes:

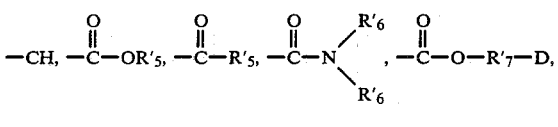

where $R'_5$ denotes a lower alkyl group, $R'_6$ denotes hydrogen or a lower alkyl group, $R'_7$ denotes an alkylene group of 1 to 4 carbon atoms and D denotes a quaternary ammonium group, A and B, which may be identical or different, represent polymethylene groups containing 2 to 20 and preferably 2 to 10 carbon atoms, which may be linear or branched, saturated or unsaturated and may contain, inserted in the main chain, one or more aromatic rings(s) such as

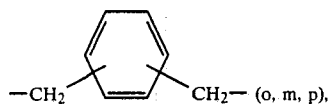  (o, m, p), and/or one or more groups:

$$-(CH_2)_n-Y_1-(CH_2)_n- \quad (VII)$$

where $Y_1$ denotes

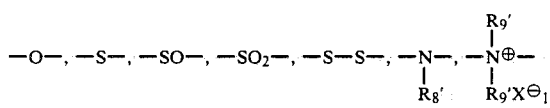

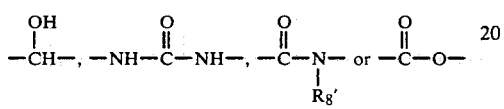

where $X^\ominus_1$ denotes an anion, preferably derived from an inorganic or organic acid, n denotes 2 or 3, $R'_8$ denotes hydrogen or a lower alkyl group and $R'_9$ denotes a lower alkyl group, or A and $R_7$ and $R_9$ form with the two nitrogen atoms to which they are attached a piperazine ring; in addition, when A denotes an alkylene or hydroxyalkylene radical which is linear or branched, saturated or unsaturated, B can denote a group:

$$-(CH_2)_{n'}-CO-D-OC-(CH_2)_{n'}- \quad (VIII)$$

in which D denotes:

(a) a glycol residue of the formula —O—Z—O— where Z denotes a linear or branched hydrocarbon radical or a group corresponding to the formula:

$$+CH_2-CH_2-O]_x-CH_2-CH_2- \quad (IX)$$

or

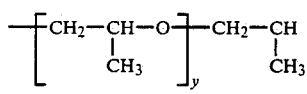

where x and y denote an integer from 1 to 4 which represents a specified and unique degree of polymerisation or an integer or decimal number from 1 to 4 which represents an average degree of polymerisation; or (b) a bis-secondary diamine residue such as a piperazine derivative; or (c) a bis-primary diamine residue of the formula

—NH—Y—NH— where Y denotes a linear or branched hydrocarbon radical or the divalent radical —CH$_2$—CH$_2$—S—S—CH$_2$—CH$_2$—; or (d) a ureylene group of the formula —NH—CO—NH—; where n' denotes the number 1 or an integer from 3 to 10; and $X'^\ominus$ denotes an anion, preferably a chloride or bromide anion.

These polymers have a molecular weight which is generally from 1,000 to 100,000.

Polymers of this type are described, in particular, in French Pat. Nos. 2,320,330, 2,270,846, 2,316,271, French Patent Applications Nos. 2,336,434 and 2,413,907 and U.S. Pat. Nos. 2,273,780, 2,375,853, 2,388,614, 2,454,547, 3,206,462, 2,261,002 and 2,271,378.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020.

The quaternised polymers of the ionene type which are particularly preferred contain the repeat units:

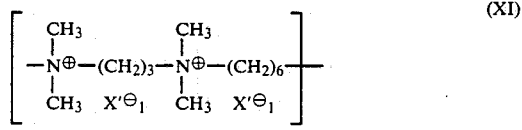 (XI)

where $X'_1^\ominus$ denotes $Cl^\ominus$ or $Br^\ominus$,

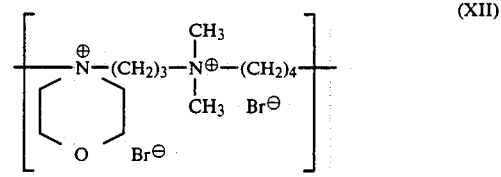 (XII)

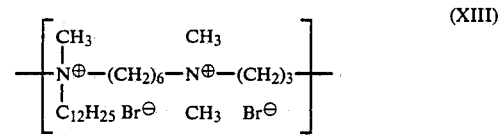 (XIII)

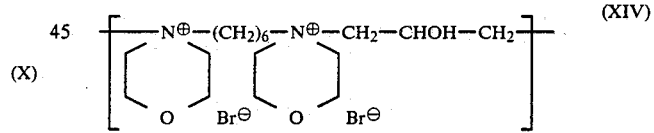 (XIV)

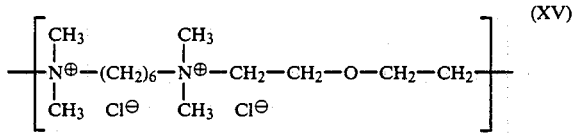 (XV)

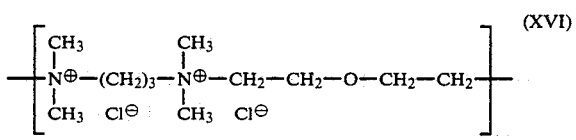 (XVI)

The preparation of these polymers is described in French Pat. No. 2,270,846 and in U.S. Pat. No. 4,217,914 of the Applicant Company.

Other particularly preferred polymers contain the following repeat units:

$$\left[-\overset{\underset{|}{CH_3}}{\overset{\oplus}{N}}-(CH_2)_3-NH-\overset{O}{\overset{||}{C}}-NH-(CH_2)_3-\overset{\underset{|}{CH_3}}{\overset{\oplus}{N}}-CH_2-CH_2-O-CH_2-CH_2-\right] \quad (XVII)$$
$$\overset{\phantom{CH_3}}{\underset{CH_3 \quad Cl^{\ominus}}{\phantom{|}}} \qquad \overset{\phantom{CH_3}}{\underset{CH_3 \quad Cl^{\ominus}}{\phantom{|}}}$$

$$\left[-\overset{\underset{|}{CH_3}}{\overset{\oplus}{N}}-(CH_2)_3-\overset{\underset{|}{CH_3}}{\overset{\oplus}{N}}-CH_2-CO-NH-(CH_2)_2-NH-CH_2-CH_2-\right]$$
$$\underset{CH_3 \quad Cl^{\ominus}}{\phantom{|}} \qquad \underset{CH_3 \quad Cl^{\ominus}}{\phantom{|}}$$

$$\left[-\overset{\underset{|}{CH_3}}{\overset{\oplus}{N}}-(CH_2)_3-\overset{\underset{|}{CH_3}}{\overset{\oplus}{N}}-CH_2-CO-NH-(CH_2)_2-NH-CO-CH_2-\right]$$
$$\underset{CH_3 \quad Cl^{\ominus}}{\phantom{|}} \qquad \underset{CH_3 \quad Cl^{\ominus}}{\phantom{|}}$$

The cationic silicone polymers present in the composition according to the invention preferably have the formula:

$$R'_a G_{3-a}-Si-(OSiG_2)_n-(OSi G_b R'_{2-b})_m-O-Si G_{3-a}R'_a$$

in which

G denotes H, phenyl, OH, $C_{1-8}$ alkyl, and preferably denotes methyl, a denotes 0 or an integer from 1 to 3 and is preferably equal to 0 b denotes 0 or 1 and is preferably equal to 1 the total (n+m) denotes a number from 1 to 2,000 and preferably from 50 to 150, n being capable of denoting zero or a number from 1 to 1,999 and preferably from 49 to 149 and m being capable of denoting a number from 1 to 2,000 and preferably from 1 to 10, R' denotes a monovalent radical of the formula $$C_q H_{2q} L$$

in which q is 2 to 8 and L denotes:
N R''—$CH_2$—$CH_2$—N(R'')$_2$
N(R'')$_2$
N$^\oplus$(R'')$_3$A$^\ominus$
N$^\oplus$(R'')$_2$H$_2$A$^\ominus$—
NR''$CH_2$—$CH_2$—N$^\oplus$R''H$_2$A$^\ominus$ in which R'' denotes H, phenyl, benzyl, a saturated monovalent hydrocarbon radical, preferably an alkyl radical containing from 1 to 20 carbon atoms and A$^-$ represents a halide ion (Cl$^-$, Br$^-$ or F$^-$).

These compounds are described in greater detail in European Patent Application No. 95,238. A polymer which is particularly preferred is that sold by the Company DOW CORNING under the name "DOW CORNING Q2 7224" which is a combination of:

(a) Trimethylsilylamodimethicone of the formula:

$$(CH_3)_3-Si-\left[O-\underset{\underset{CH_3}{|}}{\overset{\overset{CH_3}{|}}{Si}}\right]_{x''}-\left[O-\underset{\underset{\underset{\underset{NH_2}{|}}{(CH_2)_2}}{\underset{NH}{|}}}{\overset{\overset{CH_3}{|}}{\underset{(CH_2)_3}{Si}}}\right]_{y''}-OSi(CH_3)_3$$

(b) octoxynol-40 of the formula:

$C_8H_{17}$—$C_6H_4$—$(OCH_2CH_2)_n$—OH where n is 40

(c) isolaureth-6 of the formula:

$C_{12}H_{25}$—$(OCH_2CH_2)_n$OH where n is 6, and (d) glycol.

Other cationic silicone polymers which may be present in the composition according to the invention are those corresponding to the formula:

$$R_{13}-CH_2-CHOH-CH_2-\overset{\oplus}{N}(R_{12})_3 Q^\ominus$$
$$(R_{12})_3-Si-O-\left[\underset{\underset{R_{12}}{|}}{\overset{\overset{R_{12}}{|}}{Si}}-O\right]_r-\left[\underset{\underset{R_{12}}{|}}{\overset{\overset{R_{12}}{|}}{Si}}-O\right]_s-Si-(R_{12})_3$$

in which $R_{12}$ denotes a monovalent hydrocarbon radical of 1 to 18 carbon atoms, in particular an alkyl or alkenyl radical and preferably methyl, $R_{13}$ denotes a divalent hydrocarbon radical, preferably a $C_1$-$C_{18}$ alkylene radical or a divalent $C_1$-$C_{18}$ and preferably $C_1$-$C_8$ alkleneoxy radical.

Q$^-$ denotes a halide ion, preferably chloride or bromide r denotes a statistical mean value from 2 to 20 and preferably from 2 to 8.

s denotes a statistical mean value from 20 to 200 and preferably from 20 to 50.

These compounds are described in greater detail in the U.S. Pat. No. 4,185,017.

A polymer which is particularly preferred is that sold by the Company UNION CARBIDE under the name "UCAR SILICONE ALE 56", which has a flash point, according to ASTDM-93, of 60° C. and at a concentration of 35% active ingredient the viscosity at 25° C. is 11 cp and the total basic index value is 0.24 milliequivalents/gram.

The cationic silicone polymers present in the composition according to the invention are most preferably those referred to in the CTFA Dictionary, 3rd edition 1982 (CTFA Cosmetic Dictionary, published by The Cosmetic, Toiletry and Fragrance Association, Inc. 1133 Fifteenth Street NW Washington) under the name of Amodimethicone of the formula:

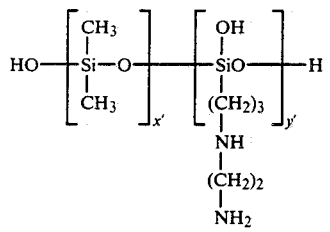

(XVIII)

where $x'$ and $y'$ are integers which depend on the molecular weight, the average molecular weight being approximately from 5,000 to 10,000.

A particularly preferred polymer is that sold under the trade name DOW CORNING 929 (DC 929) cationic emulsion by the DOW CHEMICAL COMPANY, which is a combination of "Amodimethicone" and "tallowtrimonium chloride" of the formula:

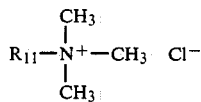

where $R_{11}$ denotes a mixture of alkenyl and/or alkyl radicals of 14 to 22 carbon atoms and derived from tallow fatty acids and "Nonoxynol 10" of the formula:

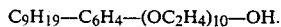

The abovementioned cationic surface-active agents are preferably present in the cosmetic hair-care composition according to the invention in proportions of from 0.05 to 7% and more preferably from 0.1 to 3% by weight of the total weight of the composition.

The water-soluble quaternary polyammonium compounds of the ionene type are preferably present in the cosmetic hair-care composition according to the invention in proportions of from 0.05 to 7% and more preferably of from 0.1 to 3% by weight of the total weight of the composition.

The cationic silicone polymers are preferably present in the cosmetic hair-care composition according to the invention in proportions of from 0.05 to 7% and more preferably from 0.1 to 3% by weight of the total weight of the composition.

A particularly preferred cosmetic hair-care composition according to the invention contains:

(a) at least one cationic surface-active agent of the formula (I):

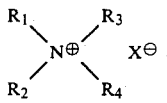

in a proportion which is from 0.5 to 1.5% of the total weight of the composition, (b) at least one quaternised polymer of the ionene type of the formula:

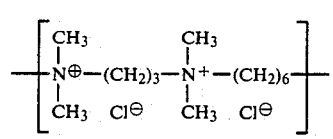

in a proportion which is from 0.1 to 0.6%, and (c) at least one silicone polymer such as DC 929 or DOW CORNING Q2 7224 of the DOW Company or such as "UCAR SILICONE ALE 56" of UNION CARBIDE in a proportion which is from 0.5 to 1.5% of the total weight of the composition.

The cosmetic hair-care compositions according to the invention are generally in the form of aqueous or aqueous-alcohol dispersions, which may be thickened or unthickened, creams, gels, aerosol foams or sprays.

In addition to the cationic surface-active agent which can be dispersed in water, the quaternised polymer of the ionene type and the silicone polymer, they may also contain adjuvants conventionally employed in cosmetics such as fragrances, colorants, preserving agents, sequestering agents, thickeners, emulsifiers, softeners and foam stabilisers, depending on the intended application.

The cosmetic hair-care compositions according to the invention may generally be applied in the form of shampoo, rinsing products to be applied before or after shampooing, before or after tinting or bleaching, before or after permanent waving or straightening, products for setting or brushing, conditioning compositions, restoring compositions and compositions for permanent-waved hair.

When the composition forms a shampoo, it also contains one or more anionic, non-ionic, amphoteric and/or zwitterionic surface-active agents, the total concentration of the surface-active agent being generally from 3 to 50% and preferably from 3 to 20% by weight of the total weight of the composition.

The pH is generally from 3 to 10.

The compositions according to the invention may also be in the form of rinses. These products may be aqueous or aqueous-alcohol dispersions, emulsions, thickened compositions or gels.

When the compositions are in the form of emulsions, they may be non-ionic or anionic.

When the compositions are in a thickened form or are gels, they contain thickeners in the presence or absence of solvents.

The thickeners which can be employed may, for example, be sodium alginate or gum arabic, cellulose derivatives such as methylcellulose, hydroxymethylcellulose, hydroxyethylcellulose, hydroxypropylcellulose, hydroxypropylmethylcellulose, guar gum or its derivatives. A thickening of the compositions may also be produced by mixing polyethylene glycol and polyethylene glycol stearate or distearate or by a mixture of a phosphoric ester and an amide.

The concentration of thickening agent is preferably from 0.5 to 30% by weight and more preferably from 0.5 to 15% by weight.

The pH of the rinses is generally from 3 to 9.

When the compositions according to the invention are in the form of products for hairdressing or styling or setting, they usually incorporate, in an aqueous or aqueous-alcohol dispersion, anti-foam agents and non-ionic polymers.

The combination according to the invention may also be employed in compositions for curling permanent-waved hair. The conventional technique for these permanent waves consists in applying, in a first stage, a composition containing a agent and then, after having rinsed the hair if appropriate, applying a composition containing an oxidising agent. According to the invention, at least one of the two compositions contains the combination such as described earlier.

When the compositions according to the present invention are distributed in the form of an aerosol foam, the propellant gasses employed to pressurize the cosmetic formulations are generally present in proportions which do not exceed 25% and preferably do not exceed 15% relative to the total weight of the composition. Examples of propellent gases which may be employed are carbon dioxide, nitrogen, nitrous oxide, volatile hydrocarbons such as butane, isobutane, propane and their mixtures, non-hydrosable chlorinated and/or fluorinated hydrocarbons such as, for example, those sold under the name FREON by the Company Du Pont de Nemours and belonging to the classes of fluorochlorohydrocarbons such as dichlorofluoromethane or Freon 12, dichlorotetrafluoroethane or Freon 114. These propellants may be employed alone or combined; mention can be made in particular of the mixture of Freon 114-12 in proportions varying between 40:60 and 80:20.

The pH of the composition according to the invention is generally from 3 to 10, depending on the intended application. It is adjusted with the aid of alkalysing or acidifying agents which are well known in the state of the art.

The invention is further illustrated with the aid of the following examples:

EXAMPLE 1

A rinsing composition having the following formulation is prepared. Cationic surface-active agent of the formula below.

$$C_8H_{17}\text{-}(C_2H_3(C_{16}H_{33})O)\text{-}(C_2H_3(CH_2OH)O)\text{-}CH_2\text{-}CHOH\text{-}CH_2\text{-}\overset{\oplus}{N}\diagdown O\diagup$$

$$\underset{CH_3SO_4^{\ominus}}{CH_3}$$

1.5 g as A.I.

cationic polymer consisting of the following repeat units:

$$\left[ \begin{array}{cc} CH_3 & CH_3 \\ | & | \\ \text{-}\overset{\oplus}{N}\text{-}(CH_2)_3\text{-}\overset{\oplus}{N}\text{-}(CH_2)_2\text{-}O\text{-}(CH_2)_2\text{-} \\ | & | \\ CH_3\ Cl^{\ominus} & CH_3\ Cl^{\ominus} \end{array} \right]$$

0.5 g as A.I.

| | |
|---|---|
| Cationic silicone polymer sold by the Company Dow Corning under the name "Cationic emulsion DC 929", having an A.I. concentration of 35% | 1.5 g as A.I. |
| NaOH q.s.(quantity sufficient for) pH 6.8 | |
| Fragrance, colorant, preserving agent, q.s. | |
| Water q.s. | 100 g |

(A.I.) stands for active ingredient).

This composition is applied to clean hair. After it has been left in place for 4 to 5 minutes, the hair is rinsed, and it then untangles easily and is soft. After drying, it remains lively and soft.

EXAMPLE 2

An after-shampoo is prepared in the form of aerosol foam, the active principle of which has the composition:

Distearyl dimethylammonium chloride 1.5 g as A.I.

Quaternary polyammonium chloride of the structure:

$$\left[ \begin{array}{c} CH_3 \\ | \\ \text{-}N^+\text{-}CH_3 \\ | \\ (CH_2)_3 \\ | \\ NH \\ | \\ C=O \\ | \\ NH \\ | \\ (CH_2)_3 \\ | \\ CH_3\text{-}N^+\text{-}CH_2CH_2OCH_2CH_2\text{-} \\ | \\ CH_3 \end{array} \right]_n, 2nCl^-$$

| | |
|---|---|
| sold under the name "MIRAPOL A 15" by the Company MIRANOL | 0.7 g as A.I. |
| Cationic silicone polymer sold by the Company Dow CORNING under the name "Cationic emulsion DC 929", at a concentration of 35% A.I. | 0.5 g as A.I. |
| NaOH q.s. pH 7.2 | |
| Fragrance, preserving agent, colorant q.s. | |
| Water q.s. | 100 g as A.I. |
| Aerosol packaging: | 90 g |
| Active principle | |
| Propellants: Freons 12/114 | 10 g |
| Total | 100 g |

The foam is applied to clean hair and left in contact for a few minutes. After being rinsed, hair untangles very easily; once dried, it is arranged with great ease.

EXAMPLE 3

An after-shampoo having the following composition is prepared:

| | |
|---|---|
| Cationic surface-active agent with the formula below: | 2.5 g as A.I. |

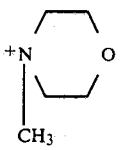

$$C_{10}H_{21}O\!-\!\!\left[C_2H_3(C_{14}H_{29})O\right]\!\!-\!\!\left[C_2H_3(CH_2OH)O\right]\!-\!CH_2\!-\!CHOH\!-\!CH_2\!-\!{}^+\!N\diagup\!\diagdown\!O$$

with CH$_3$ on N, counterion CH$_3$SO$_4^-$

| | |
|---|---|
| Cationic polymer consisting of repeat units of the formula: | 0.4 g as A.I. |

$$-{}^+\!\!\underset{\underset{CH_3\ Br^-}{|}}{\overset{\overset{CH_3}{|}}{N}}\!-\!(CH_2)_3\!-\!{}^+\!\!\underset{\underset{CH_3\ Br^-}{|}}{\overset{\overset{CH_3}{|}}{N}}\!-\!(CH_2)_6-\quad (XI)$$

| | |
|---|---|
| Cationic silicone polymer sold by the Company Dow Corning under the name "Cationic emulsion DC 929", having an A.I. concentration of 35% | 1 g as A.I. |
| Mixture of cetylstearyl alcohol and of cetylstearyl alcohol oxyethyleneated with 15 moles of ethylene oxide, sold under the name "SINNOWAX AO" by the Company Henkel | 4 g as A.I. |
| Mixture of fatty alcohol and oxyethyleneated products sold under the name "POLA-WAX GP 200" by the Company CRODA | 1 g as A.I. |
| Hydroxyethylcellulose sold under the name "Cellosize QP 4400 H" by the Company UNION CARBIDE | 0.5 g as A.I. |
| Citric acid q.s. pH 5.5 | |
| Fragrance, colorant, preserving agent, q.s. | |
| Water q.s. | 100 g |

This composition is applied in the same way as in Examples 1 and 2. The wet hair is light; when dried, it is shiny and the ends are smoother.

EXAMPLES 4–8

Example 3 is repeated with the exception that the cationic polymer of the formula (XI) is replaced, respectively, by the same quantity of polymer of the formula (XII), (XIII), (XIV), (XV) or (XVI).

Similar results are obtained.

EXAMPLE 9

An after-shampoo having the following composition is prepared:

| | |
|---|---|
| Stearyl dimethylbenzylammonium chloride | 1 g as A.I. |
| Cationic polymer consisting of repeat units of the formula: | 0.5 g as A.I. |

$$-\!\!\underset{\underset{CH_3\ Cl^{\ominus}}{|}}{\overset{\overset{CH_3}{|}}{{}^{\oplus}\!N}}\!-\!(CH_2)_3\!-\!\underset{\underset{CH_3\ Cl^{\ominus}}{|}}{\overset{\overset{CH_3}{|}}{{}^{\oplus}\!N}}\!-\!((CH_2)_6-$$

| | |
|---|---|
| Cationic silicone polymer sold by the Company Dow Corning under the name "Cationic emulsion DC 929", at a concentration of 35% A.I. | 0.6 g as A.I. |
| Hydroxypropylated and quaternised guar gum sold under the name "Jaguar C 13 S" by the Company CELANESE | 0.2 g as A.I. |
| NaOH q.s. pH = 6 | |
| Fragrance, colorant, preserving agent, q.s. | |
| Water q.s. | 100 g |

This rinsing composition facilitates the untangling of wet hair and confers softness and suppleness. Dried hair is silky, light and well-behaved.

EXAMPLE 10

The lotion which is not rinsed and has the following composition is prepared:

| | |
|---|---|
| quaternary ammonium salt of the formula | |

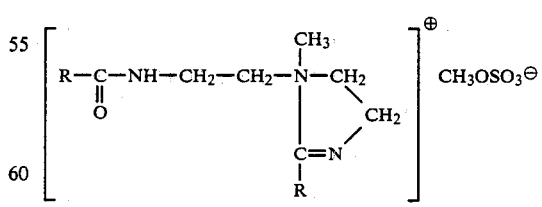

$$\left[\begin{array}{c}R\!-\!\underset{\underset{O}{\overset{\|}{C}}}{}\!-\!NH\!-\!CH_2\!-\!CH_2\!-\!\underset{\underset{R}{\overset{|}{C=N}}}{\overset{\overset{CH_3}{|}}{N}}\!\diagup\!\!\!\!\!\diagdown\!\!\!\begin{array}{c}CH_2\\ |\\ CH_2\end{array}\right]^{\oplus}\ CH_3OSO_3^{\ominus}$$

| | |
|---|---|
| R denotes a mixture of alkenyl and/or alkyl radicals having from 14 to 22 carbon atoms derived from tallow fatty acids, sold by REWO under the name "REWOQUAT W 7500" at a concentration of 78% of A.I. | 6.0 g as A.I. |
| NaCl | 2.5 g |
| Cationic polymer of the formula: | 1.5 g |

-continued $$\left[ -\overset{CH_3}{\underset{\underset{CH_3\ Cl^{\ominus}}{|}}{\overset{|}{\oplus}}}-(CH_2)_3-\overset{CH_3}{\underset{\underset{CH_3Cl^{\ominus}}{|}}{\overset{|}{\oplus}}}-CH_2-CO-NH-(CH_2)_2NH-CO-CH_2- \right]$$

The preparation of this polymer is described in French Pat. No. 2,413,907

| | |
|---|---|
| Cationic silicone polymer sold by the Company UNION CARBIDE under the name "UCAR SILICONE ALE 56" at a concentration of 35% A.I. | 1.0 g as A.I. |
| Ethyl alcohol | 10.0 g |
| NaOH q.s. pH = 6 | |
| Water q.s. | 100.0 g |

The composition is applied to clean and damp hair before it is set. After drying, sensitised hair untangles easily, is lively, soft and shiny up to the ends.

EXAMPLE 11

A setting lotion having the following composition is prepared:

Cationic polymer of the formula:      0.5 g as A.I.

$$\left[ -\overset{\oplus}{\underset{\underset{CH_3}{|}}{\overset{CH_3Cl^{\ominus}}{|}}}N{+}CH_2{\overset{}{)_3}}\overset{CH_3\ Cl^{\ominus}}{\underset{\underset{CH_3}{|}}{\overset{|}{\oplus}}}N-CH_2-CO-NH-CH_2{\overset{}{)_2}}NH-CO-CH_2- \right]$$

The preparation of this polymer is described in French Pat. No. 2,413,907.

| | |
|---|---|
| Quaternary ammonium salt of the formula: | |

$$\left[ \begin{array}{c} R-C-NH-CH_2-CH_2-N-CH_2 \\ \overset{\|}{O} \quad\quad\quad\quad\quad\quad\quad | \quad\quad\ \backslash \\ \quad\quad\quad\quad\quad\quad\quad\quad\quad\quad CH_3 \ \ CH_2 \\ \quad\quad\quad\quad\quad\quad\quad\quad\quad\quad\quad\quad\quad \ \ / \\ \quad\quad\quad\quad\quad\quad\quad\quad\quad\quad\quad C=N \\ \quad\quad\quad\quad\quad\quad\quad\quad\quad\quad\quad | \\ \quad\quad\quad\quad\quad\quad\quad\quad\quad\quad\quad R \end{array} \right]^{\oplus} CH_3OSO_3^{\ominus}$$

| | |
|---|---|
| R denotes a mixture of alkenyl and/or alkyl radicals having from 14 to 22 carbon atoms, derived from tallow fatty acids, sold by REWO under the name of REWOQUAT W 7500 at a concentration of 78% A.I. | 0.5 g as A.I. |
| Cationic silicone polymer sold by the Company Union Carbide under the name "UCAR SILICONE ALE 56" at a concentration of 35% A.I. | 0.2 g as A.I. |
| Polyvinylpyrrolidone/vinyl acetate (60/40) copolymer | 1.0 g as A.I. |
| Ethyl alcohol | 10.0 g |
| 2-Amino-2-methylpropan-1-ol q.s. pH = 8.5 | |
| Water q.s. | 100.0 g |

This lotion is applied to clean and damp hair. After drying, and particularly in the case of sensitised hair, it permits easy untangling and well-behaved arrangement. The hair is lively, soft and shiny up to the ends.

EXAMPLE 12

The same setting lotion as that of Example 11 is prepared, with the exception that the cationic polymer is replaced with the same weight, as A.I., of a polymer of the formula:

$$\left[ -\overset{CH_3}{\underset{\underset{CH_3\ Br^{\ominus}}{|}}{\overset{|}{\oplus}}}-(CH_2)_3-\overset{CH_3}{\underset{\underset{CH_3\ Br^{\ominus}}{|}}{\overset{|}{\oplus}}}-(CH_2)_6- \right]$$

The same result is obtained as with the lotion of Example 11.

EXAMPLE 13

An after-shampoo having the following composition is prepared:

| | |
|---|---|
| Stearamidopropyl dimethyl (myristylacetate) ammonium chloride sold by the Company VAN DYCK under the name "CERAPHYL 70" at a concentration of 70% of A.I. | 1.0 g as A.I. |
| Cationic polymer consisting of repeat units of the formula: | 0.5 g |

$$\left[ -\overset{CH_3}{\underset{\underset{CH_3\ Cl^{\ominus}}{|}}{\overset{|}{\oplus}}}-(CH_2)_3-\overset{CH_3}{\underset{\underset{CH_3\ Cl^{\ominus}}{|}}{\overset{|}{\oplus}}}-(CH_2)_6- \right]$$

| | |
|---|---|
| Cationic silicone polymer sold under the name "DOW CORNING Q2 7224" at a concentration of 35% of A.I. by the Company Dow Corning | 0.6 g |
| Hydroxypropylated and quaternised guar gum sold under the name "JAGUAR C 13S" by the Company CELENESE | 0.2 g |
| Fragrance, colorant, preserving agent q.s. | |
| Water q.s. | 100.0 g |

This rinsing composition facilitates the untangling of wet hair. The dried hair is silky, light and well-behaved.

EXAMPLE 14

Hair is permanently waved by applying to the hair the following reducing composition:

| | |
|---|---|
| Thioglycolic acid | 8 g |
| Aqueous Ammonia q.s. | pH 7 |
| Ammonium bicarbonate | 6.4 g |
| Distearyldimethylammonium chloride | 0.2 g |
| Cationic polymer prepared according to French Patent 2,270,846, containing recurring units of formula: | 3 g |

$$\left[ -\overset{CH_3}{\underset{\underset{CH_3\ Cl^{\ominus}}{|}}{\overset{|}{\oplus}}}-(CH_2)_3-\overset{CH_3}{\underset{\underset{CH_3\ Cl^{\ominus}}{|}}{\overset{|}{\oplus}}}-(CH_2)_6- \right]$$

| | |
|---|---|
| Cationic silicone polymer sold by DOW CORNING under the name "Cationic Emulsion CD 929" at a concentration of 35. A.I. | 0.5 g |
| Oleic alcohol oxyethylated by 20 mols of ethylene oxide | 1 g |
| Perfume q.s. | |

-continued

| | |
|---|---|
| Water q.s. | 100 g |

The hair is then rolled up on curlers and the composition is left to act for 5 to 15 minutes. It is then carefully rinsed and the following oxidising composition is applied:

| | |
|---|---|
| Phenylacetin | 0.1 g |
| Citric acid | 0.3 g |
| Nonylphenol oxyethylated with 9 moles of ethylene oxide | 1 g |
| Hydrogen peroxide q.s. | 8 volumes |
| Colourant, perfume q.s. | |
| Water q.s. | 100 g |

The oxidising composition is left to act for 10 minutes. The hair is then rinsed and dried.

The wet hair combs out easily and is silky to the touch. After drying the hair is brilliant, is silky to the touch, and combs out easily.

We claim:

1. A cosmetic composition for the treatment and care of hair, comprising (a) 0.05 to 7% by weight of a cationic surface-active agent which can be dispersed in water, (b) 0.05% to 7% by weight of a water-soluble quaternary polyammonium compound (c) 0.05 to 7% by weight of a cationic silicone polymer selected from the group consisting of: (I) having the formula:

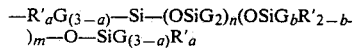

where
G denotes H, phenyl, OH, or $C_1$–$C_8$-alkyl,
a denotes zero or an integer from 1 to 3,
p denotes zero or 1
n denotes zero or a number from 1 to 1,999
m denotes a number from 1 to 2,000
the total (n+m) denoting a number from 1 to 2,000
R' denotes a monovalent radical of the formula $C_qH_{2q}L$ in which q is 2 to 8 and L denotes:
—NR"—$CH_2$—$CH_2$—NR"$_2$
—N(R")$_2$
—$\overset{+}{N}$(R")$_3$A$^-$
—$\overset{+}{N}$(R")H$_2$A$^-$
—NR"$CH_2$—$CH_2$—$\overset{+}{N}$R"H$_2$A$^-$ in which R" denotes H, phenyl, benzyl, or an alkyl radical having from 1 to 20 carbon atoms,
A$^-$ represents Cl$^-$, Br$^-$, I$^-$ or F$^-$,
(II) having the formula

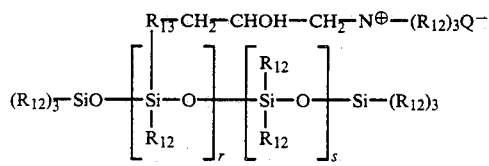

in which
$R_{12}$ denotes a monovalent hydrocarbon radical of 1 to 18 carbon atoms $R_{13}$ denotes a $C_1$–$C_{18}$-alkylene or $C_1$–$C_{18}$-alkyleneoxy divalent radical
Q$^-$ denotes a Cl$^-$ or Br$^-$ ion
r denotes a number from 2 to 20 and represents a statistical mean value
S denotes a number from 20 to 200 and represents a statistical mean value, and (III)

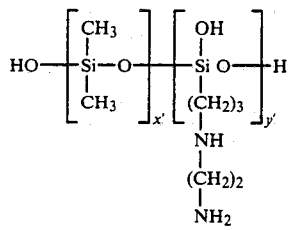

where x' and y' are integers which depend on the molecular weight, the mean molecular weight being from 5,000 to 10,000 and (d) an aqueous or aqueous-alcoholic dispersion carrier; wherein the composition has a pH of from 3 to 10.

2. A composition according to claim 1 containing from about 0.1 to 3.0% by weight of said cationic surface active agent, from about 0.1 to 3.0% by weight of said water-soluble quaternary polyammonium compound and from about 0.1 to 3.0% by weight of said cationic silicone polymer.

3. A composition according to claim 1 in which the cationic surface-active agent (a) has the formula:

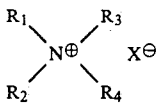

in which
(1)
$R_1$ denotes a group of the formula:

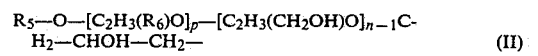

where $R_5$ denotes a linear or branched, saturated or unsaturated aliphatic radical of 4 to 20 carbon atoms;
$R_6$ denotes:
(i) an alkyl radical of 4 to 20 carbon atoms,
(ii) a linear or branched alkoxymethyl radical, the alkoxy moiety having from 4 to 20 carbon atoms,
(iii) a linear alkenyloxy radical of 4 to 20 carbon atoms;
p denotes an integer or decimal number from 1 to 2.5 and represents a statistical mean value;
n denotes an integer or decimal number from 2 to 20 and represents a statistical mean value;
$R_2$ denotes an alkyl or hydroxyalkyl radical having from 1 to 3 carbon atoms;
$R_3$ and $R_4$, which may be identical or different, denote an alkyl or hydroxyalkyl radical having from 1 to 3 carbon atoms or $R_3$ and $R_4$ form, together with the nitrogen atom to which they are attached, a 5- or 6-membered heterocyclic ring;
X$^\ominus$ denotes an anion; or
(2)
$R_2$ and $R_3$ denotes methyl, $R_1$ and $R_4$ then having the following meanings;

(i) $R_1$ and $R_4$ denote a linear saturated aliphatic radical of 12 to 22 carbon atoms or an aliphatic radical of 14 to 22 carbon atoms;
(ii) $R_1$ denotes a linear saturated aliphatic radical of 14 to 22 carbon atoms and $R_4$ denotes methyl or benzyl;
(iii) $R_1$ denotes an alkylamidopropyl radical, the alkyl moiety having from 14 to 22 carbon atoms and $R_4$ denotes an alkylacetone group in which the alkyl moiety has 12 to 16 carbon atoms;
$X^\ominus$ denotes an anion; or (3) $R_1$ denotes an alkylamidoethyl and/or alkenylamidoethyl group in which the alkyl and/or alkenyl group contains from 14 to 22 carbon atoms, $R_2$ and $R_3$ form, with the nitrogen atom to which they are attached, a substituted heterocyclic ring of the 4,5-dihydroimidazole type;

$R_4$ denotes an alkyl group of 1 to 4 carbon atoms; and $X^-$ denotes a $CH_3SO_4^-$ anion.

4. A composition according to claim 3 in which the cationic surface-active agent (a) has the formula (I) in which:
(a)
$R_1$ denotes

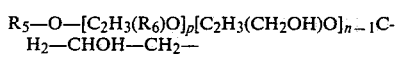
$R_5-O-[C_2H_3(R_6)O]_p[C_2H_3(CH_2OH)O]_{n-1}C-H_2-CHOH-CH_2-$ (II)

where $R_5$ denotes $C_8H_{17}$ or $C_{10}H_{21}$,
$R_6$ denotes $C_{14}H_{29}$ or $C_{16}H_{33}$,
p denotes the number 1,
n denotes an integer or decimal number from 2 to 5,
$R_2$ denotes a methyl radical,
$R_3$ and $R_4$, together with the nitrogen atom to which they are attached, denote a morpholino heterocyclic ring,
$X^\ominus$ denotes $CH_3SO_4^\ominus$ or $CH_3SO_3^\ominus$; or
(b)
$R_1$ denotes

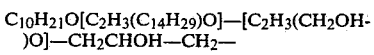
$C_{10}H_{21}O[C_2H_3(C_{14}H_{29})O]-[C_2H_3(CH_2OH)O]-CH_2CHOH-CH_2-$ $R_2$ denotes a methyl radical,
$R_3$ and $R_4$, together with the nitrogen atom to which they are attached, denote a morpholino heterocyclic ring,
$X^\ominus$ denotes $CH_3SO_3^\ominus$; or
(c)
$R_1$ denotes

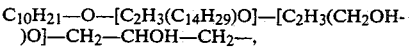
$C_{10}H_{21}-O-[C_2H_3(C_{14}H_{29})O]-[C_2H_3(CH_2OH)O]-CH_2-CHOH-CH_2-$, $R_2$ denotes a methyl radical,
$R_3$ and $R_4$, together with the nitrogen atom to which they are attached, denote a morpholino heterocyclic ring,
$X^\ominus$ denotes $CH_3SO_3^\ominus$; or
(d)
$R_1$ and $R_4$ each denote a mixture of alkenyl and/or alkyl radicals derived from tallow fatty acids and of 14 to 22 carbon atoms,
$R_2$ and $R_3$ denote a methyl radical,
$X^\ominus$ denotes $Cl^-$;
(e)
$R_1$ denotes an alkylamidoethyl group and/or an alkenylamidoethyl group where the alkyl and/or alkenyl radical contains from 14 to 22 carbon atoms, derived from tallow fatty acids, $R_2$ and $R_3$ form, together with the nitrogen atom to which they are attached, a 2-alkyl (derived from tallow fatty acids) 4,5-dihydroimidazole heterocyclic ring; $R_4$ denotes an alkyl group of 1 to 4 carbon atoms.

5. A composition according to claim 1, in which the quaternary polyammonium compound (b) has repeat units of formula:

in which $R_7$, $R_8$, $R_9$ and $R_{10}$, which are identical or different, represent aliphatic, alicyclic or arylaliphatic radicals containing at most 20 carbon atoms or lower hydroxyaliphatic radicals, or $R_7$ and $R_8$, and $R_9$ and $R_{10}$, together or separately, form with the nitrogen atoms to which they are attached heterocyclic rings which may contain a second hetero-atom other than nitrogen, or $R_7$, $R_8$, $R_9$ and $R_{10}$ represent a group:

in which $R'_3$ denotes hydrogen or a lower alkyl group and $R'_4$ denotes:

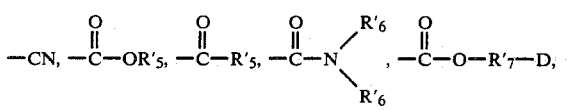

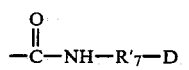

where $R'_5$ denotes a lower alkyl group, $R'_6$ denotes hydrogen or a lower alkyl group, $R'_7$ denotes an alkylene group of 1 to 4 carbon atoms and D denotes a quaternary ammonium group, A and B, which may be identical or different, represent polymethylene groups containing 2 to 20 carbon atoms which may be linear or branched, saturated or unsaturated and may contain, inserted in the main chain, one or more aromatic ring(s) such as

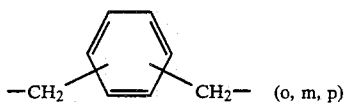

one or more groups;

$-(CH_2)_n-Y_1-(CH_2)_n-$ (VII)

where $Y_1$ denotes $-O-$, $-S-$, $-SO-$, $-SO_2-$, $-S-S-$,

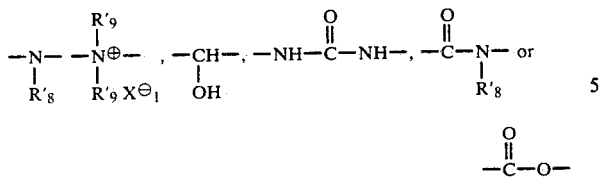

where $X^{\ominus}_1$ denotes an anion, n denotes 2 or 3, $R'_8$ denotes hydrogen or a lower alkyl group and $R'_9$ denotes a lower alkyl group, or A and $R_7$ and $R_9$ form with the two nitrogen atoms to which they are attached a piperazine ring; in addition, when A denotes an alkylene or hydroxyalkylene radical, which is linear or branched, saturated or unsaturated, B can denote a group:

$$-(CH_2)_{n'}-CO-D-OC-(CH_2)_{n'}- \quad (VIII)$$

in which D denotes:

(a) a glycol residue of the formula $-O-Z-O-$ where Z denotes a linear or branched hydrocarbon radical or a group corresponding to the formula:

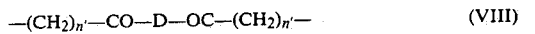

or

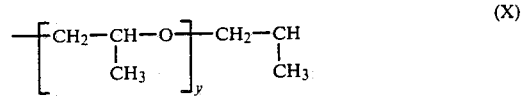

where x and y denote an integer from 1 to 4 which represents a specified and unique degree of polymerisation or an integer or decimal number from 1 to 4 which represents an average degree of polymerisation; or (b) a bis-secondary diamine residue; or
(c) a bis-primary residue of the formula $-NH-Y-NH-$ where Y denotes a linear or branched hydrocarbon radical or the divalent radical $-CH_2-CH_2-S-S-CH_2-CH_2-$; or
(d) a ureylene group of the formula $-NH-CO-NH-$ where n' denotes the number 1 or an integer from 3 to 10, and $X^{\ominus}$ denotes an anion.

6. A composition according to claim 5, in which the quaternary polyammonium compound (b) has a molecular weight from 1,000 to 100,000.

7. A composition according to claim 5 in which the quaternary polyammonium compound (b) contains the repeat units;

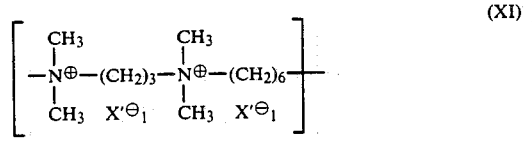

where $X'_1^-$ denotes $Cl^-$ or $Br^-$,

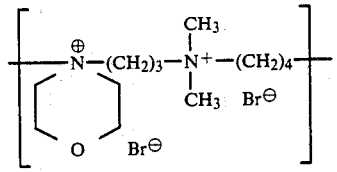 (XII)

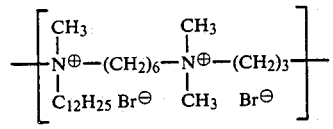 (XIII)

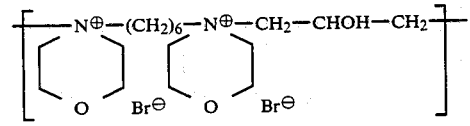 (XIV)

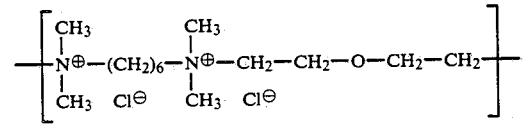 (XV)

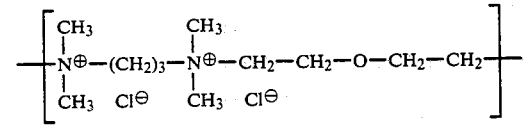 (XVI)

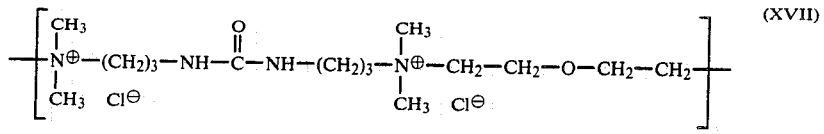

(XVII)

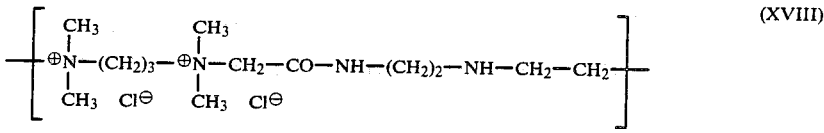

(XVIII)

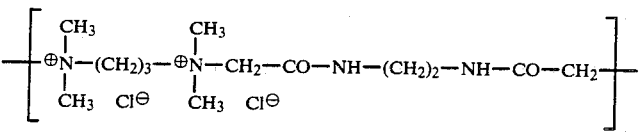

8. A composition according to claim 1 in which the cationic silicone polymer is a combination of:
(a) Trimethylsilylamodimethicone of the formula:

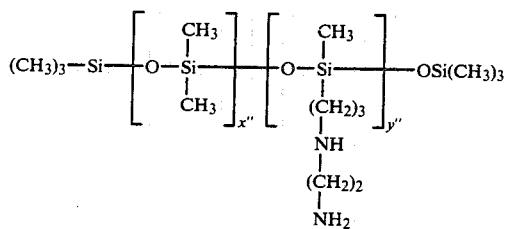

(b) $C_8H_{17}-C_6H_4-(OCH_2CH_2)_n-OH$ where n is 40,
(c) $C_{12}H_{25}-(OCH_2-CH_2)_nOH$ where n is 6; and
(d) glycol.

9. A composition according to claim 1, which contains the silicone polymer (c) Amidomethicone of the formula:

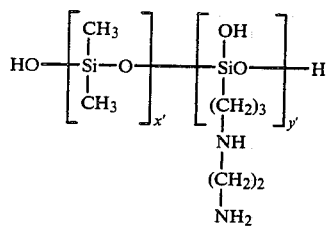

(XVIII)

where x' and y' have the meanings indicated in claim 18, together with
(i) a trimethyl alkyl ammonium chloride of the formula:

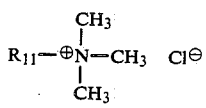

where $R_{11}$ denotes a mixture of alkenyl and/or alkyl radicals of 14 to 22 carbon atoms derived from tallow fatty acids; and
(ii) polyethoxylated nonylphenol of the formula $C_9H_{19}-C_6H_4-(OC_2H_4)_{10}-OH$.

10. A composition according to claim 3, which contains a cationic surface-active agent (a) of the formula:

(I)

where $R_1$ to $R_4$ and $X^-$ have the meanings given in claim 2, at least one quaternary polyammonium compound (b) of the formula:

$$-\left[\begin{array}{c}CH_3\\|\\N^\oplus-(CH_2)_3-N^\oplus-(CH_2)_6\\|\\CH_3\ Cl^\ominus\quad CH_3\ Cl^\ominus\end{array}\right]-$$

(XI)

and at least one silicone polymer (c) combined with a trimethyl alkyl ammonium chloride and a polyethoxylated nonylphenol of formula $C_9H_{19}-(OC_2H_4)_{10}-OH$.

11. A composition according to claim 1, which is in the form of a shampoo, a rinse to be applied before or after shampooing, before of after tinting or bleaching, before or after permanent-waving or straightening; a product for setting or blow-drying, a conditioning composition, or a composition for permanent-waved hair.

12. A composition according to claim 1, which also contains one or more adjuvants which are: an anionic, non-ionic, amphoteric and/or zwitterionic surface-active agent, a fragrance, a colorant, a preserving agent, a sequestering agent, a thickener, an emulsifier, a softener, a foam stabiliser, or a propellant.

13. A process for treating hair, in which an effective amount of the composition according to claim 1 is applied to the hair.

* * * * *